(12) United States Patent
Fleming, III (10) Patent No.: US 7,854,757 B2
(45) Date of Patent: Dec. 21, 2010

(54) BIODEGRADABLE INTRALUMENAL DEVICE

(75) Inventor: James A. Fleming, III, Bethlehem, PA (US)

(73) Assignee: Cordis Corporation, Bridgewater, NJ (US)

( * ) Notice: Subject to any disclaimer, the term of this patent is extended or adjusted under 35 U.S.C. 154(b) by 535 days.

(21) Appl. No.: 10/931,163

(22) Filed: Aug. 31, 2004

(65) Prior Publication Data
US 2005/0033413 A1 Feb. 10, 2005

Related U.S. Application Data

(63) Continuation of application No. 10/374,211, filed on Feb. 26, 2003.

(51) Int. Cl.
*A61F 2/06* (2006.01)
(52) U.S. Cl. .................................................. 623/1.15
(58) Field of Classification Search ............... 623/1.15, 623/1.16, 1.17
See application file for complete search history.

(56) References Cited

U.S. PATENT DOCUMENTS

| | | | |
|---|---|---|---|
| 5,192,307 A | 3/1993 | Wall | |
| 5,733,330 A | 3/1998 | Cox | |
| 5,766,239 A | 6/1998 | Cox | |
| 5,911,732 A | 6/1999 | Hojeibane | |
| 5,938,682 A | 8/1999 | Hojeibane et al. | |
| 5,997,563 A | 12/1999 | Kretzers | |
| 6,022,371 A | 2/2000 | Killion | |
| 6,033,436 A | 3/2000 | Steinke et al. | |
| 6,066,167 A | 5/2000 | Lau et al. | |
| 6,083,258 A | 7/2000 | Yadav | |
| 6,129,755 A | 10/2000 | Mathis et al. | |
| 6,156,062 A | 12/2000 | McGuinness | |
| 6,171,334 B1 | 1/2001 | Cox | |
| 6,174,316 B1 | 1/2001 | Tuckey et al. | |
| 6,251,134 B1 | 6/2001 | Alt et al. | |
| 6,540,777 B2 * | 4/2003 | Stenzel | 623/1.16 |
| 6,709,453 B2 | 3/2004 | Pinchasik et al. | |
| 6,709,454 B1 | 3/2004 | Cox et al. | |
| 2002/0111671 A1 | 8/2002 | Stenzel | |

FOREIGN PATENT DOCUMENTS

| | | |
|---|---|---|
| DE | 19728337 A | 1/1999 |
| DE | 199 05 756 A1 | 2/1999 |
| EP | 1266638 A | 12/2002 |
| EP | 1452152 A | 9/2004 |
| WO | WO 99/010897 A | 1/1999 |
| WO | WO 00/59405 A1 | 10/2000 |
| WO | WO 01/30271 A2 | 5/2001 |
| WO | WO 02/062268 | 8/2002 |
| WO | WO 02/065949 A | 8/2002 |
| WO | WO 04060213 A1 | 7/2004 |

OTHER PUBLICATIONS

European Search Report EP 05252657 dated Sep. 6, 2005.
European Search Report No. EP 02253789 dated Jan. 16, 2003.

* cited by examiner

*Primary Examiner*—Todd E Manahan
*Assistant Examiner*—Katherine M Dowe
(74) *Attorney, Agent, or Firm*—Louis J. Capezzuto (57) ABSTRACT

A biodegradable intralumenal device that is capable of drug delivery. The device has circular hoops connected by one or more flexible links defining a substantially cylindrical configuration capable of having a closed configuration and an open configuration. Each hoop mateably connects with or interlocks with an adjacent hoop in the open configuration in order to retain this configuration subsequent to delivery of the device.

51 Claims, 4 Drawing Sheets

BIODEGRADABLE INTRALUMENAL DEVICE

This is a continuation application of Ser. No. 10/374,211 filed Feb. 26, 2003 which is incorporated herein by reference.

FIELD OF THE INVENTION

The present invention relates, in general, to intralumenal medical devices, and, more particularly, two a new and useful stent having interlocking elements for stenting a vessel.

BACKGROUND ART

A stent is commonly used as a tubular structure left inside the lumen of a duct to relieve an obstruction. Commonly, stents are inserted into the lumen in a non-expanded form and are then expanded autonomously (or with the aid of a second device) in situ. When used in coronary artery procedures for relieving stenosis, stents are placed percutaneously through the femoral artery. In this type of procedure, stents are delivered on a catheter and are either self-expanding or, in the majority of cases, expanded by a balloon. Self-expanding stents do not need a balloon to be deployed. Rather the stents are constructed using metals with spring-like or superelastic properties (i.e., Nitinol), which inherently exhibit constant radial support. Self-expanding stents are also often used in vessels close to the skin (i.e., carotid arteries) or vessels that can experience a lot of movement (i.e., popliteal artery). Due to a natural elastic recoil, self-expanding stents withstand pressure or shifting and maintain their shape.

As mentioned above, the typical method of expansion for balloon expanded stents occurs through the use of a catheter mounted angioplasty balloon, which is inflated within the stenosed vessel or body passageway, in order to shear and disrupt the obstructions associated with the wall components of the vessel and to obtain an enlarged lumen.

In addition, balloon-expandable stents are available either pre-mounted or unmounted. A pre-mounted system has the stent already crimped on a balloon, while an unmounted system gives the physician the option as to what combination of devices (catheters and stents) to use. Accordingly, for these types of procedures, the stent is first introduced into the blood vessel on a balloon catheter. Then, the balloon is inflated causing the stent to expand and press against the vessel wall. After expanding the stent, the balloon is deflated and withdrawn from the vessel together with the catheter. Once the balloon is withdrawn, the stent stays in place permanently, holding the vessel open and improving the flow of blood.

In the absence of a stent, restenosis may occur as a result of elastic recoil of the stenotic lesion. Although a number of stent designs have been reported, these designs have suffered from a number of limitations. Some of these limitations include design limitations resulting in low radial strength, decrease in the length of the stent upon deployment, i.e. foreshortening, and high degree of axial compression experienced by the stent.

Accordingly, to date, there have not been any stent designs, that specifically address these drawbacks in an efficient and cost effective manner.

BRIEF SUMMARY OF THE INVENTION

The present invention relates to an apparatus and method for stenting a vessel in conjunction with a particular new and useful stent having a lattice of interconnecting elements defining a substantially cylindrical configuration. The lattice has a first open end and a second open end wherein the lattice is movable between a closed configuration and an open configuration.

The lattice comprises a plurality of adjacent hoops wherein each hoop is separated from another hoop in the closed configuration and each hoop interlocks with another hoop in the open configuration.

Each hoop comprises a plurality of loops. And, each hoop further comprises a plurality of struts connected to the loops.

At least one loop of one hoop comprises a male end and at least one loop of another hoop comprises a female end. The male end is separated from the female end when the lattice is in the closed configuration. The male end is connectably mated to the female end when the lattice is moved to the open configuration thereby locking the stent lattice in the open configuration.

Thus, the male end of at least one loop of one hoop and the female end of at least one loop of another hoop form a locked joint when the lattice is moved into the open configuration thereby locking the stent in the open configuration.

The lattice further comprises at least one flexible link or a plurality of flexible links connected between adjacent hoops. The flexible links comprise various shapes such as a sinusoidal shaped, straight or linear shape, or a substantially S-shaped or Z-shaped pattern. At least one flexible link is connected between loops of adjacent hoops of the lattice.

Additionally, the plurality of struts and the loops define at least one pre-configured cell. Preferably, the lattice comprises a plurality of pre-configured cells defined by the plurality of struts and the loops of the lattice.

Additionally, the plurality of struts and the loops also define at least one partial cell. In a preferred embodiment in accordance with the present invention, the plurality of struts and the loops define a plurality of partial cells. A partial cell is defined by the plurality of struts and the loops when the lattice is in the closed configuration.

Additionally, the plurality of struts and the loops define at least one formed cell. In a preferred embodiment in accordance with the present invention, the plurality of struts and the loops of the stent lattice define a plurality of formed cells. A formed cell is defined by the plurality of struts and the loops when the lattice is moved into the open configuration (locked configuration).

The male end of the at least one loop of one hoop has a substantially convex configuration. The female end of at least one loop of another hoop has a substantially concave configuration. In accordance with the present invention, alternative forms, shapes or configurations for the male end and female end respectively are also contemplated herein.

In accordance with one embodiment of the present invention, each pre-configured cell has a substantially diamond shape. Other shapes for the pre-configured cell are also contemplated by the present invention, and thus, the pre-configured cell may take the form of any desired shape.

Additionally, the stent lattice further comprises a drug coating or a drug and polymer coating combination. In one embodiment according to the present invention the drug is rapamycin. In an alternative embodiment in accordance with the present invention, the drug is paclitaxel. Other drugs and drug polymer combinations are also contemplated by the present invention and examples are provided later in this disclosure.

The stent of the present invention is directed toward both a balloon actuated stent and a self-expanding stent. The stent is made of any suitable material. In one embodiment, the stent is made of an alloy such as stainless steel. In another preferred embodiment, the stent is made of a nickel titanium (Nitinol)

alloy. Moreover, this material or any other super-elastic alloy is suitable for the stent according to the present invention. In these self-expanding stent embodiments, the stent is a crush recoverable stent.

BRIEF DESCRIPTION OF THE DRAWINGS

The novel features of the invention are set forth with particularity in the appended claims. The invention itself, however, both as to organization and methods of operation, together with further objects and advantages thereof, may be best understood by reference to the following description, taken in conjunction with the accompanying drawings in which:

DETAILED DESCRIPTION OF THE INVENTION

In FIGS. 1-4, a stent 100 that is an expandable prosthesis for a body passageway is illustrated. It should be understood that the terms "stent" and "prosthesis" are interchangeably used to some extent in describing the present invention, insofar as the method, apparatus, and structures of the present invention may be utilized not only in connection with an expandable intraluminal vascular graft for expanding partially occluded segments of a blood vessel, duct or body passageways, such as within an organ, but may so be utilized for many other purposes as an expandable prosthesis for many other types of body passageways. For example, expandable prostheses may also be used for such purposes as: (1) supportive graft placement within blocked arteries opened by transluminal recanalization, but which are likely to collapse in the absence of internal support; (2) similar use following catheter passage through mediastinal and other veins occluded by inoperable cancers; (3) reinforcement of catheter created intrahepatic communications between portal and hepatic veins in patients suffering from portal hypertension; (4) supportive graft placement of narrowing of the esophagus, the intestine, the ureters, the uretha, etc.; (5) intraluminally bypassing a defect such as an aneurysm or blockage within a vessel or organ; and (6) supportive graft reinforcement of reopened and previously obstructed bile ducts. Accordingly, use of the term "prosthesis" encompasses the foregoing usages within various types of body passageways, and the use of the term "intraluminal graft" encompasses use for expanding the lumen of a body passageway. Further in this regard, the term "body passageway" encompasses any lumen or duct within the human body, such as those previously described, as well as any vein, artery, or blood vessel within the human vascular system.

The stent 100 is an expandable lattice structure made of any suitable material which is compatible with the human body and the bodily fluids (not shown) with which the stent 100 may come into contact. The lattice structure is an arrangement of interconnecting elements made of a material which has the requisite strength and elasticity characteristics to permit the tubular shaped stent 100 to be moved or expanded from a closed (crimped) position or configuration shown in FIGS. 1 and 2 to an expanded or open position or configuration shown in FIGS. 2 and 3. Some examples of materials that are used for the fabrication of the stent 100 include silver, tantalum, stainless steel, gold, titanium or any type of plastic material having the requisite characteristics previously described. Based on the interlocking design of the stent 100 (greater detail provided later in this disclosure), when the stent 100 is deployed or expanded to its open position, even materials that tend to recoil to a smaller diameter or exhibit crushing or deformation-like properties are used for the stent 100 in accordance with the present invention. These are materials that are not used in traditional (prior art) stent designs. Some examples of these non-traditional stent materials that are used for the stent 100 in accordance with the present invention include deformable plastics, plastics that exhibit crushing or recoil upon deployment of the stent or polymers such as biodegradable polymers. Thus, the stent 100 in accordance with the present invention is also made of these type of plastics or polymers to include biodegradable polymers. Additionally, the biodegradable polymers used as material for the stent 100 can be drug eluting polymers capable of eluting a therapeutic and/or pharmaceutical agent according to any desired release profile.

In one embodiment, the stent is fabricated from 316L stainless steel alloy. In a preferred embodiment, the stent 100 comprises a superelastic alloy such as nickel titanium (NiTi, e.g., Nitinol). More preferably, the stent 100 is formed from an alloy comprising from about 50.5 to 60.0% Ni by atomic weight and the remainder Ti. Even more preferably, the stent 100 is formed from an alloy comprising about 55% Ni and about 45% Ti. The stent 100 is preferably designed such that it is superelastic at body temperature, and preferably has an Af temperature in the range from about 24° C. to about 37° C. The superelastic design of the stent 100 makes it crush recoverable and thus suitable as a stent or frame for any number of vascular devices for different applications.

Figure 3:
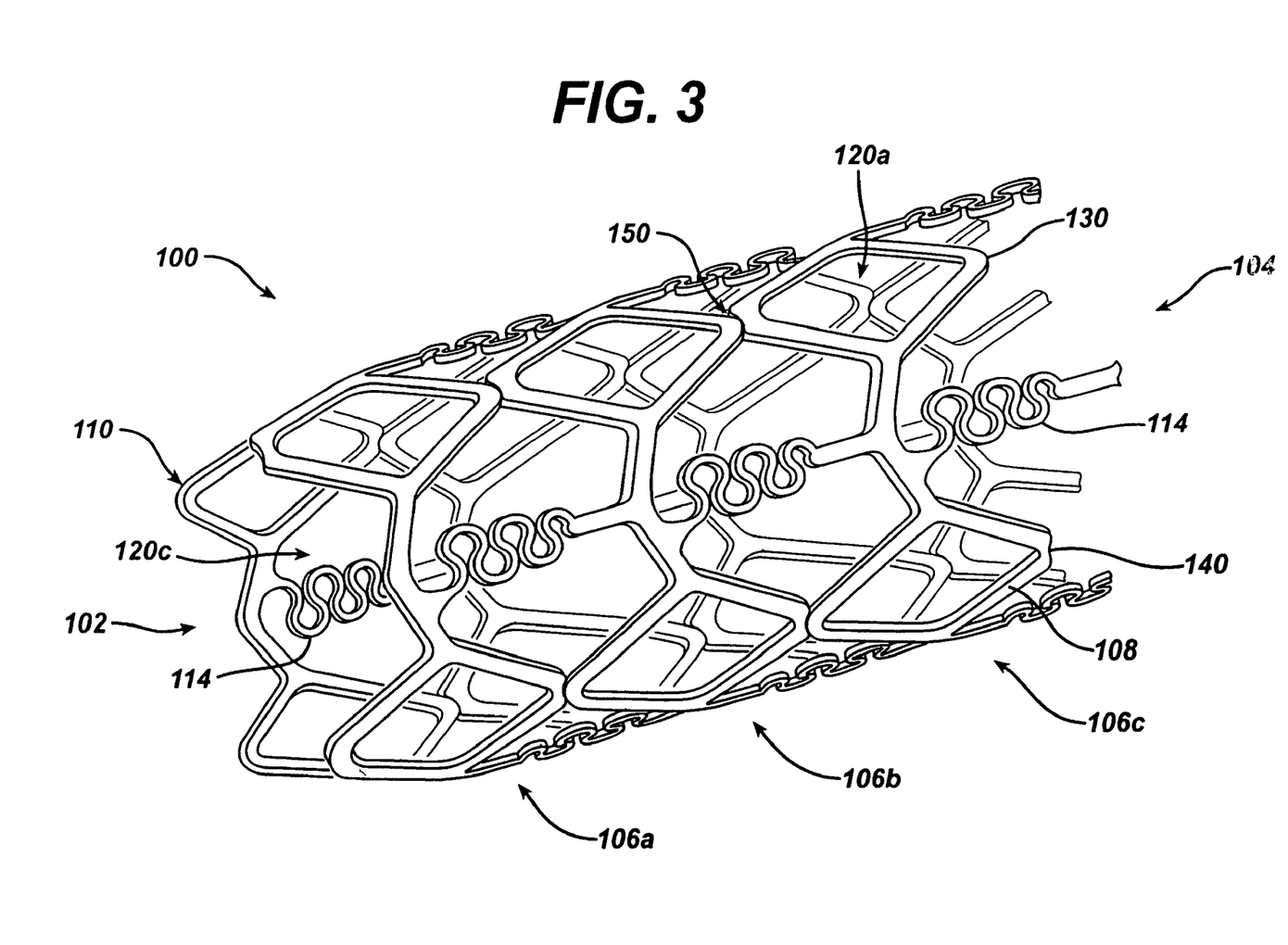
FIG. 3 is a perspective view of the stent of FIG. 1 in an open configuration in accordance with the present invention.

The stent 100 comprises a tubular configuration formed by a lattice of interconnecting elements defining a substantially cylindrical configuration and having front and back open ends 102, 104 and defining a longitudinal axis extending therebetween. In its closed configuration, the stent 100 has a first diameter for insertion into a patient and navigation through the vessels and, in its open configuration, a second diameter, as shown in FIG. 3, for deployment into the target area of a vessel with the second diameter being greater than the first diameter. The stent 100 comprises a plurality of adjacent hoops 106a-106h extending between the front and back ends 102, 104. The stent 100 comprises any combination or number of hoops 106. The hoops 106a-106h include a plurality of longitudinally arranged struts 108 and a plurality of loops 110 connecting adjacent struts 108. Adjacent struts 108 or loops 110 are connected at opposite ends by flexible links 114 which can be any pattern such as sinusoidal shape, straight (linear) shape or a substantially S-shaped or Z-shaped pattern. The plurality of loops 110 have a substantially curved configuration.

The flexible links 114 serve as bridges, which connect adjacent hoops 106a-106h at the struts 108 or loops 110. Each flexible link comprises two ends wherein one end of each link 114 is attached to one strut 108 or one loop 110 on one hoop 106a and the other end of the link 114 is attached to one strut 108 or one loop 110 on an adjacent hoop 106b, etc.

Figure 1:
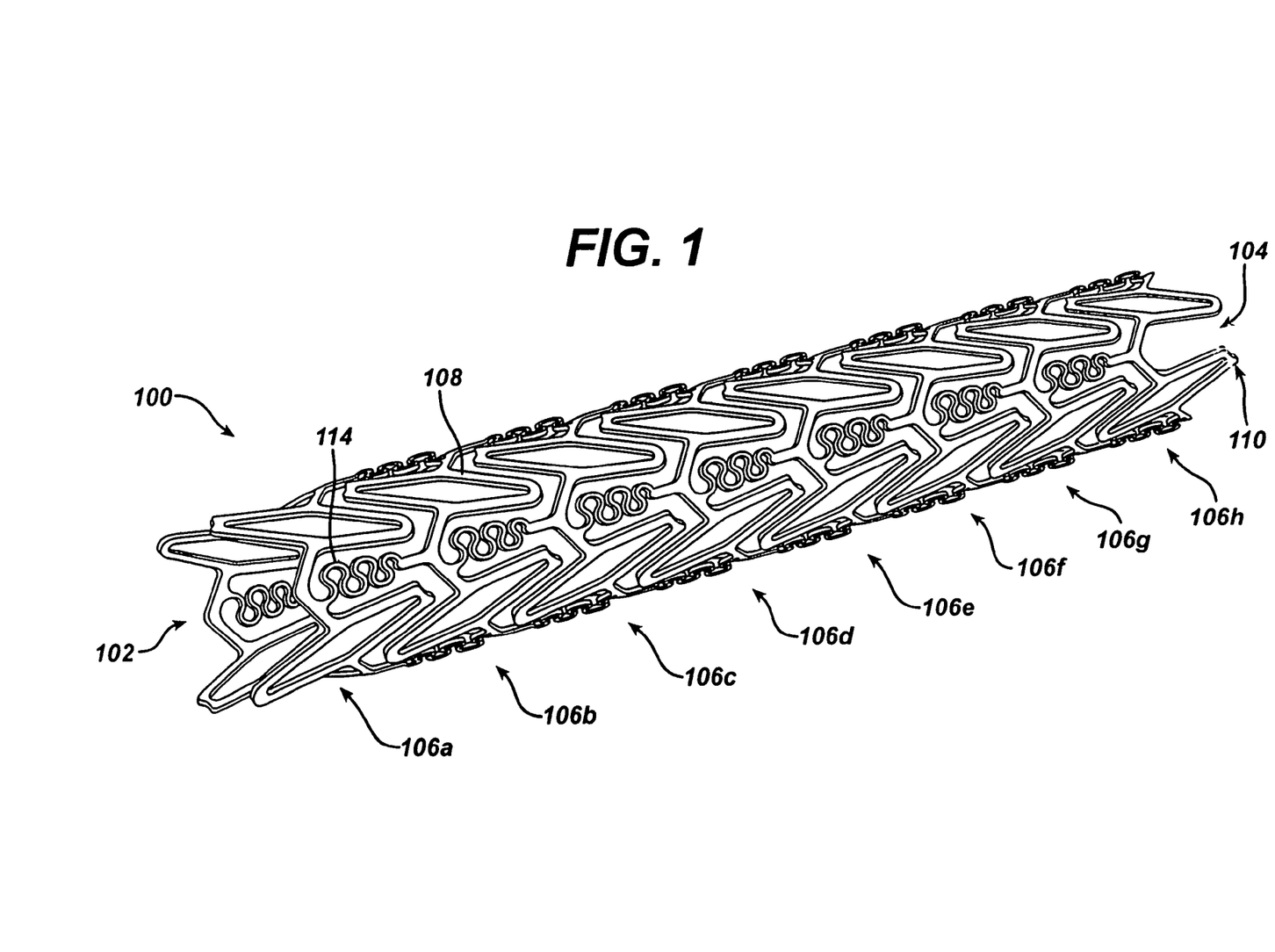
FIG. 1 is a perspective view of a of a stent in a closed-configuration in accordance with the present invention.

The above-described geometry better distributes strain throughout the stent 100, prevents metal to metal contact where the stent 100 is bent, and minimizes the opening between the features of the stent 100; namely, struts 108, loops 110 and flexible links 114. The number of and nature of the design of the struts, loops and flexible links are important design factors when determining the working properties and fatigue life properties of the stent 100. It was previously thought that in order to improve the rigidity of the stent, struts should be large, and thus there should be fewer struts 108 per hoop 106a-106h. However, it is now known that stents 100 having smaller struts 108 and more struts 108 per hoop 106a-106h improve the construction of the stent 100 and provide greater rigidity. Preferably, each hoop 106a-106h has between twenty-four (24) to thirty-six (36) or more struts 108. It has been determined that a stent having a ratio of number of struts per hoop to strut length which is greater than four hundred has increased rigidity over prior art stents which typically have a ratio of under two hundred. The length of a strut is measured in its compressed state (closed configuration) parallel to the longitudinal axis of the stent 100 as illustrated in FIG. 1.

FIG. 3 illustrates the stent 100 in its open or expanded state. As may be seen from a comparison between the stent 100 configuration illustrated in FIG. 1 and the stent 100 configuration illustrated in FIG. 3, the geometry of the stent 100 changes quite significantly as it is deployed from its unexpanded state (closed or crimped configuration/position) to its expanded state (open or expanded configuration/position). As the stent 100 undergoes diametric change, the strut angle and strain levels in the loops 110 and flexible links 114 are affected. Preferably, all of the stent features will strain in a predictable manner so that the stent 100 is reliable and uniform in strength. In addition, it is preferable to minimize the maximum strain experienced by the struts 108, loops 110 and flexible links 114 since Nitinol properties are more generally limited by strain rather than by stress. The embodiment illustrated in FIGS. 1-4 has a design to help minimize forces such as strain.

Figure 2:
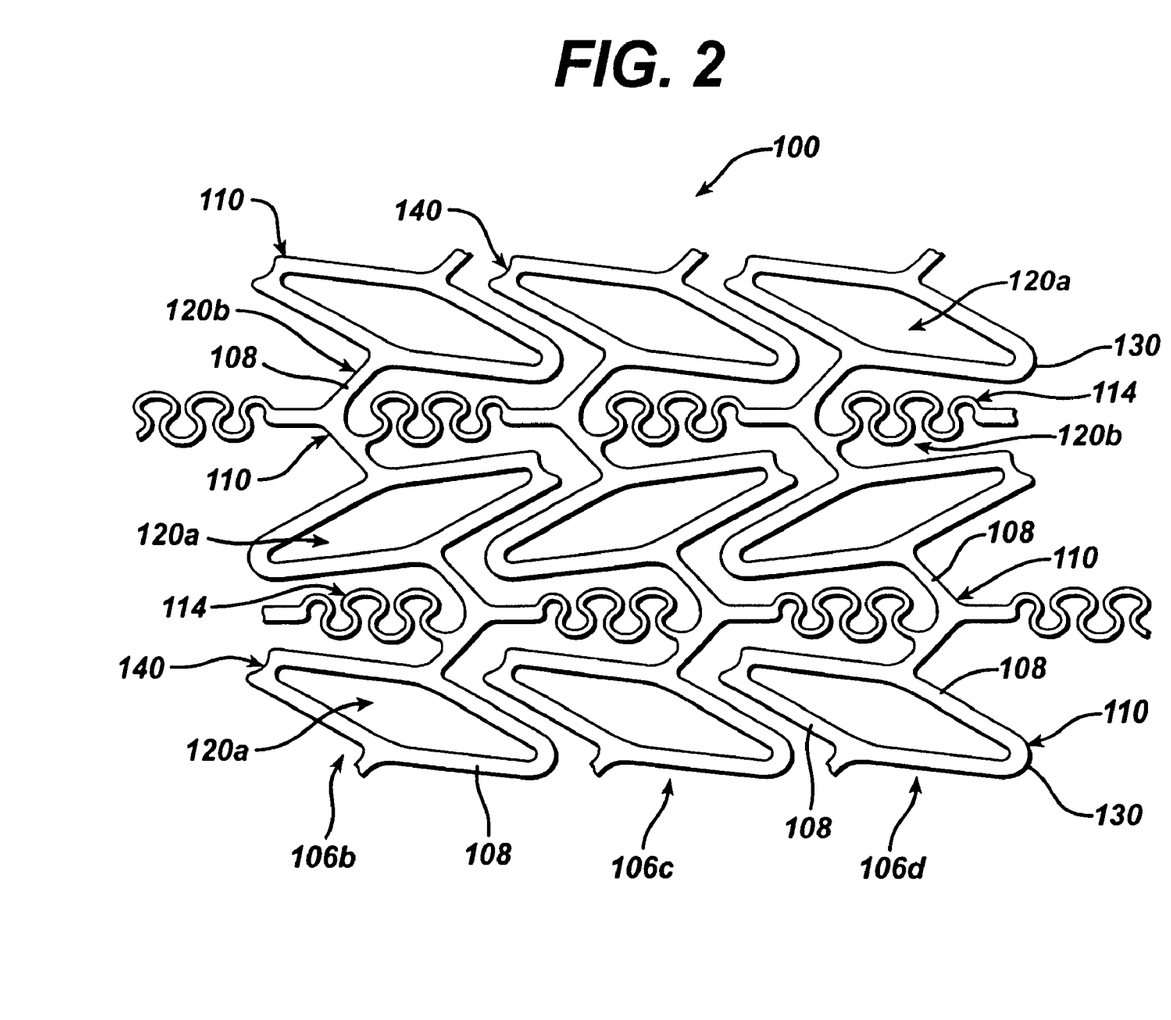
FIG. 2 is a partial side plan view of the stent of FIG. 1A in the closed configuration in accordance with the present invention.

As best illustrated in FIG. 2, the stent 100, in the closed-configuration (crimped configuration wherein the stent 100 is crimped on the stent delivery device such as a catheter), has a plurality of pre-configured cells 120a. Each pre-configured cell 120a is defined by the struts 108 and loops 110 connected to each other respectively thereby defining an open area in the stent lattice 100. This open area is a space identified as the pre-configured cell 120a.

Each hoop 106a-106h has one or more (or a plurality of) pre-configured cells 120a. In one embodiment according to the present invention, the pre-configured cell 120a is a diamond-shaped area or space. However, it is contemplated in accordance with the present invention that the pre-configured cell 120a take the form of any desired alternative shape.

Additionally, the stent lattice 100 also includes at least one (or a plurality of) partial cells 120b. Each partial cell 120b is defined by struts 108 and one loop 110 of the respective hoops 106a-106h. In one embodiment according to the present invention, the partial cell 120b defines a semi-enclosed area or space having an open end in direct communication with a loop 110 from an adjacent hoop 106a-106h. In this embodiment according to the present invention, the flexible link 114 connects adjacent hoops, for example hoop 106b to hoop 106c, by having one end of flexible link 114 connected to an inner surface of loop 110 of a partial cell 120b of the hoop 106b and the opposite end of the flexible link 114 connected to loop 110 of the adjacent hoop 106c. Thus, in this embodiment, the flexible link 114 extends from one end of the partial cell 120b, for instance, of hoop 106b and extends through the semi-enclosed area of the partial cell 120b and is connected to loop 110 of the adjacent hoop 106c. In this embodiment according to the present invention, the flexible links 114 are connected between adjacent hoops 106a-106h by extension through the partial cells 120b. Additionally, the partial cell 120b is not only a semi-enclosed area or space defined by struts 108 and one loop 110 of each hoop 106, but the partial cell 120b may take the form of any desired semi-enclosed shape.

In this embodiment according to the present invention, each partial cell 120b of the stent lattice 100 exists while the stent 100 is in its crimped state or closed configuration, i.e. crimped to the delivery device such as a catheter.

Moreover, in one embodiment according to the present invention, each pre-configured cell 120a has one loop 110 terminating in a male end 130 and the other loop defining the pre-configured cell 120a terminating in a female and 140. Thus, in this embodiment in accordance with the present invention, the male end 130 of one loop 110 and the female end 140 of the other loop 110 of the pre-configured cell 120a are positioned opposite each other thereby defining opposite ends of the pre-configured cell 120a, for example opposite-ends of the diamond-shaped area in this embodiment.

In one embodiment in accordance with the present invention, the male end 130 has a substantially convex configuration and the female end 140 has a substantially concave configuration. In general, the female end 140 is designed such that it is shaped to receive and mateably connect with the male end 130. Accordingly, in this embodiment, the substantially concave surface of the female end 140 mateably connects with the substantially convex shape of the male end 130 when the stent lattice 100 is moved to the open configuration or state (deployed or expanded state) such as shown in FIGS. 3 and 4.

Figure 4:
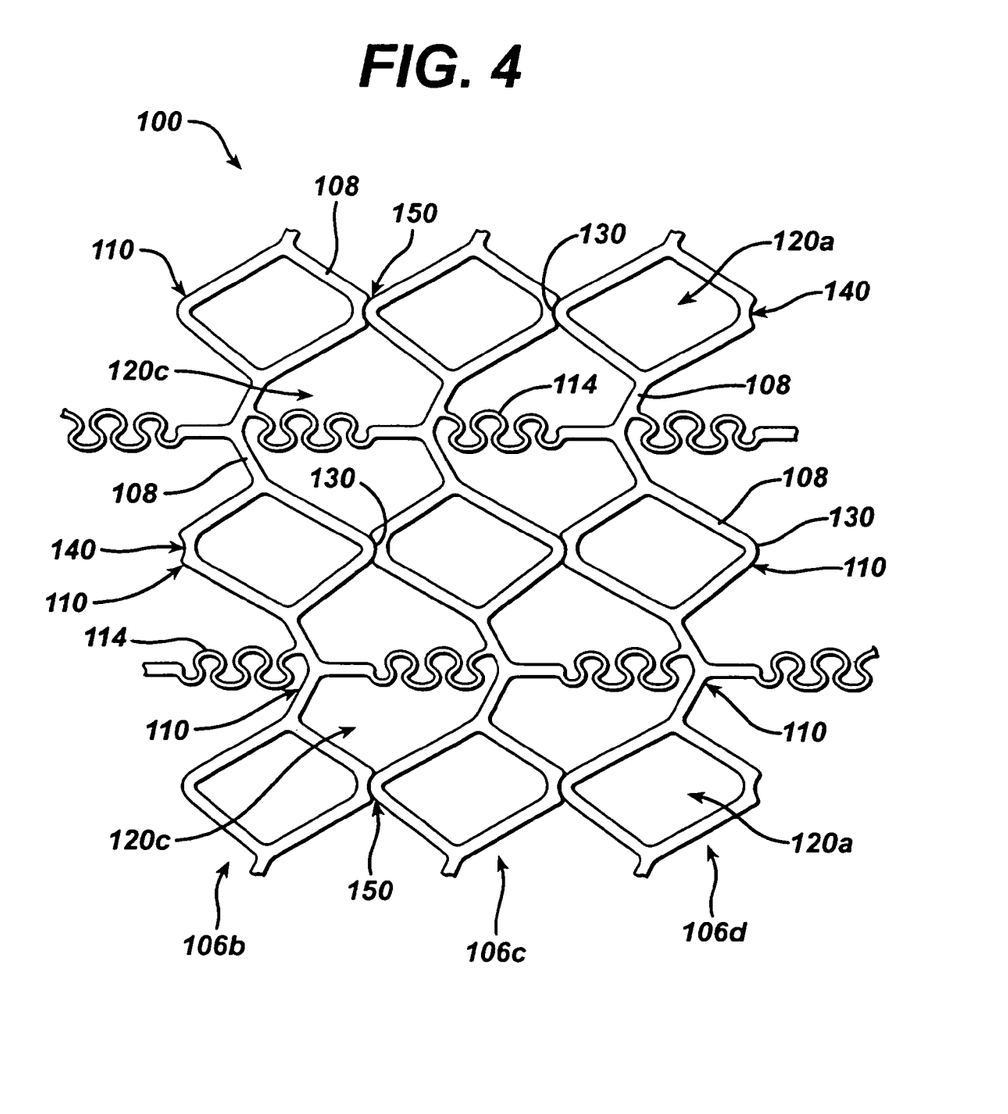
FIG. 4 is a partial side view of the stent of FIG. 1 in the open configuration in accordance with the present invention.

As best illustrated in FIG. 4, when the stent lattice 100 is deployed or expanded to its open position or configuration, the male end 130 of the loop 110 of one hoop 106, for example 106b, mateably connects with the female end 140 of an opposite loop 110 of an adjacent hoop, for example 106c, thereby forming a locked joint 150. The male end 130 and the female end 140 may take the form of any desired shape or configuration that permits the male end 130 to mateably connect with the female end 140 in order to form the locked joint 150. For example, the male end 130 and the female end 140 may be shaped respectively in order to form portions of a dove-tail such that the locked joint 150 has or forms a dove-tail configuration. Other shapes for the male end 130 and female end 140 forming the locked joint 150 are also contemplated herein.

Accordingly, when the stent lattice 100 is deployed or expanded to the open position (open configuration of the stent 100), adjacent hoops 106a-106h interlock with each other at the newly formed joints 150 mateably connecting adjacent hoops 106a-106h. For example, when the stent lattice 100 is moved to its open configuration, the hoop 106b mateably connects or interlocks with the adjacent hoop 106c and the hoop 106c interlocks with the adjacent hoop 106d, etc. Thus, the points of interlocking or mateable connection are located at the newly formed locked joint 150 between each pair of adjacent hoops 106 as shown. Thus, each locked joint 150 is formed by at least one loop 110 of one hoop 106 (for example 106b, wherein the male end 130 of this loop 110 mateably connects with the female end 140 of another loop 110), i.e. an adjacent loop on an adjacent hoop 106, for example loop 110 on the hoop 106c which is directly opposed from the male end 130 of loop 110 of the hoop 106b. Therefore, the adjacent hoops 106a-106h, are mateably connected to or locked to each other respectively at each locked joint 150 formed in a manner such as described above.

Upon the mateable connection or linking of the male end 130 to the female end 140 (on the loops 110 of adjacent hoops 106), a formed cell 120c is created or formed between adjacent locked joints 150 form by a pair of interlocking, adjacent hoops 106, for example, 106a and 106b, etc. Each formed cell 120c is a fully enclosed area or space defined by the struts 108 loops 110 and locked joints 150 formed by the adjacent hoops 106, i.e. linking of hoop 106a to hoop 106b, linking of hoop 106b to adjacent hoop 106c, etc. Accordingly, the partial cell 120b (FIG. 2) of the stent lattice 100 in its crimped configuration, becomes the formed cell 120c when linked or coupled by the locked joint 150 between adjacent hoops 106 as shown in FIG. 4.

In accordance with the present invention, the stent 100 has flexible links 110 that may be on one or more of the following components of the stent lattice: the hoops 106a-106h, the loops 110, and/or the struts 108. Moreover, the components of the stent lattice, i.e. hoops, loops, struts and flexible links, have drug coatings or drug and polymer coating combinations that are used to deliver drugs, i.e. therapeutic and/or pharmaceutical agents including: antiproliferative/antimitotic agents including natural products such as vinca alkaloids (i.e. vinblastine, vincristine, and vinorelbine), paclitaxel, epidipodophyllotoxins (i.e. etoposide, teniposide), antiobiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP)I-$I_b III_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); antiinflammatory; such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF) platelet derived growth factor (PDGF), erythropoetin; angiotensin receptor blocker; nitric oxide donors; anti-sense oligonucleotides and combinations thereof; cell cycle inhibitors, mTOR inhibitors, and growth factor signal transduction kinase inhibitors. It is important to note that one or more of the lattice components (e.g. hoops, loops, struts and flexible links) are coated with one or more of the drug coatings or drug and polymer coating combinations. Additionally, as mentioned above, the stent 100 is alternatively made of a polymer material itself such as a biodegradable material capable of containing and eluting one or more drugs, in any combination, in accordance with a specific or desired drug release profile.

The method of utilizing the stent 100 according to the present invention includes first identifying a location, for example, a site within the vessel in a patient's body for deployment of the stent 100. Upon identifying the desired deployment location, for example a stenotic lesion or vulnerable plaque site, a delivery device, such as a catheter carrying the stent 100 crimped to a distal end of the catheter such that the stent 100 is in its closed configuration, is inserted within the vessel in the patient's body. The catheter is used to traverse the vessel until reaching the desired location (site) wherein the distal end of the catheter is positioned at the desired location (site), for instance the lesion, within the vessel. At this point, the stent 100 is deployed to its open configuration by expanding the stent 100 such as by inflation if the stent 100 is a balloon expandable stent or by uncovering or release of the stent 100 if the stent 100 is a self-expanding (crush recoverable) type stent. If a cover is utilized to further protect and secure the stent 100 to the catheter distal end when the stent 100 is a self-expanding stent, the cover is removed from the distal end of the catheter prior to expansion of the stent 100, for instance, through use of an expandable member such as an inflatable balloon.

Upon expanding the stent 100 to its open configuration, the expandable member (balloon) is then collapsed, for instance through deflation of the expandable member, whereby the catheter is removed from the deployment site of the vessel and patient's body altogether.

As mentioned previously, the unique design of the stent 100, i.e. the interlocking of adjacent hoops 106 upon deployment of the stent 100, allows for a wide array of materials, not previously used with prior art stents, to be used with the stent 100 in accordance with the present invention. These include materials normally prone to crushing, deformation or recoil upon deployment of the stent. These materials include plastics and polymers to include biodegradable polymers such as drug eluting polymers.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An intralumenal device comprising:
   a first substantially circular hoop having a closed configuration and an expanded configuration;
   a second substantially circular hoop having a closed configuration and an expanded configuration adjacent to said first hoop; and
   at least one flexible link connecting said first and second hoops wherein said first and second hoops are separated from each other in the closed configuration and rotate to mateably interlock with each other in the expanded configuration, the first and second hoops each comprise a plurality of loops and a plurality of struts connected to said loops to define a plurality of pre-configured cells, at least one loop of a first pre-configured cell in the first hoop comprises a male end and at least one loop of an adjacent second pre-configured cell in the second hoop comprises a female end, wherein the male end is separated from the female end when said hoops are in the closed configuration and wherein the male end is mateably connected to the female end when said first and second pre-configured cells rotate in the same direction such that said hoops are in the expanded configuration; and wherein the first substantially circular hoop, the second substantially circular hoop and the at least one flexible link are made of a material that is normally prone to crushing, deformation or recoil in the expanded configuration.

2. The device according to claim 1, wherein the male end of the at least one loop of the first hoop and the female end of the at least one loop of the second hoop form a locked joint when said hoops are in the expanded configuration.

3. The device according to claim 1, wherein the male end has a substantially convex configuration.

4. The device according to claim 3, wherein the female end has a substantially concave configuration.

5. The device according to claim 1, wherein the device is made of a biodegradable polymer.

6. The device according to claim 5, wherein the biodegradable polymer is a drug eluting polymer.

7. The device according to claim 6, further comprising a second drug.

8. The device according to claim 6, wherein said drug is rapamycin.

9. The device according to claim 6, wherein said drug is paclitaxel.

10. The device according to claim 5, further comprising a first therapeutic agent.

11. The device according to claim 10, wherein said first agent is incorporated into said biodegradable polymer and capable of eluting therefrom.

12. The device according to claim 11, wherein said first agent is rapamycin.

13. The device according to claim 11, wherein said first agent is paclitaxel.

14. The device according to claim 10, further comprising a second agent in combination with said first agent.

15. The device according to claim 14, wherein said first agent is rapamycin.

16. The device according to claim 14, wherein said first agent is paclitaxel.

17. The device according to claim 5, wherein said device further comprises a drug coating.

18. The device according to claim 17, further comprising a second drug.

19. The device according to claim 17, wherein said drug is rapamycin.

20. The device according to claim 17, wherein said drug is paclitaxel.

21. The device according to claim 5, wherein said device further comprises a drug and polymer coating combination.

22. The device according to claim 21, further comprising a second drug.

23. The device according to claim 21, wherein said drug is rapamycin.

24. The device according to claim 21, wherein said drug is paclitaxel.

25. The device according to claim 1, wherein the at least one pre-configured cell has a substantially diamond shape.

26. A intralumenal device comprising:
two or more substantially circular adjacent hoops each having a closed configuration and an expanded configuration; and at least one flexible link disposed between and connecting each of said adjacent hoops wherein said adjacent hoops are separated from each other in the closed configuration and rotate to mateably interlock with each other in the expanded configuration, all of the two or more substantially circular adjacent hoops each comprise a plurality of loops and a plurality of struts connected to said loops to define a plurality of pre-configured cells, at least one loop of a first pre-configured cell in a first hoop comprises a male end and at least one loop of an adjacent second pre-configured cell in an adjacent second hoop comprises a female end, wherein the male end is separated from the female end when said hoops are in the closed configuration and wherein the male end is mateably connected to the female end when said first and second pre-configured cells rotate in the same direction such that said hoops are in the expanded configuration; and wherein the two or more substantially circular adjacent hoops and the at least one flexible link are made of a material that is normally prone to crushing, deformation or recoil in the expanded configuration.

27. The device according to claim 26, wherein the male end of the at least one loop of the first hoop and the female end of the at least one loop of the second hoop form a locked joint when said hoops are in the expanded configuration.

28. The device according to claim 26, wherein the male end has a substantially convex configuration.

29. The device according to claim 28, wherein the female end has a substantially concave configuration.

30. The device according to claim 26, wherein the device is made of a biodegradable polymer.

31. The device according to claim 30, wherein the biodegradable polymer is a drug eluting polymer.

32. The device according to claim 31, further comprising a second drug.

33. The device according to claim 31, wherein said drug is rapamycin.

34. The device according to claim 31, wherein said drug is paclitaxel.

35. The device according to claim 30, further comprising a first therapeutic agent.

36. The device according to claim 35, wherein said first agent is incorporated into said biodegradable polymer and capable of eluting therefrom.

37. The device according to claim 36, wherein said first agent is rapamycin.

38. The device according to claim 36, wherein said first agent is paclitaxel.

39. The device according to claim 35, further comprising a second agent in combination with said first agent.

40. The device according to claim 39, wherein said first agent is rapamycin.

41. The device according to claim 39, wherein said first agent is paclitaxel.

42. The device according to claim 30, wherein said device further comprises a drug coating.

43. The device according to claim 42, further comprising a second drug.

44. The device according to claim 42, wherein said drug is rapamycin.

45. The device according to claim 42, wherein said drug is paclitaxel.

46. The device according to claim 30, wherein said device further comprises a drug and polymer coating combination.

47. The device according to claim 46, further comprising a second drug.

48. The device according to claim 46, wherein said drug is rapamycin.

49. The device according to claim 46, wherein said drug is paclitaxel.

50. The device according to claim 26, wherein the at least one pre-configured cell has a substantially diamond shape.

51. An intralumenal device comprising:
- a first substantially circular hoop having a closed configuration and an expanded configuration;
- a second substantially circular hoop having a closed configuration and an expanded configuration adjacent to said first hoop; and
- at least one flexible link connecting said first and second hoops, each of said first and second hoops comprising a plurality of loops and a plurality of struts defining a plurality of pre-configured cells, at least one loop of a first pre-configured cell of the first substantially circular hoop comprises a male end and at least one loop of a second pre-configured cell of the second substantially circular hoop comprises a female end, wherein the male end is misaligned from the female end when said first and second hoops are in the closed configuration and the male end is mateably connected to and aligned with the female end when said first and second pre-configured cells rotate in the same direction such that said hoops are in the expanded configuration; and wherein the first substantially circular hoop, the second substantially circular hoop and the at least one flexible link are made of a material that is normally prone to crushing, deformation or recoil in the expanded configuration.

* * * * *